ent [19] [11] 3,983,120
Beverung et al. [45] Sept. 28, 1976

| [54] | PROCESS FOR THE PREPARATION OF OPTIONALLY SUBSTITUTED 1,2,3,5-TETRAHYDROIMIDAZO[2,1-b] QUINAZOLIN-2-ONES | | |
|---|---|---|---|
| [75] | Inventors: | Warren Neil Beverung, Minoa; Richard Anthony Partyka, Liverpool, both of N.Y. | |
| [73] | Assignee: | Bristol-Myers Company, New York, N.Y. | |
| [22] | Filed: | Nov. 6, 1974 | |
| [21] | Appl. No.: | 521,305 | |
| [52] | U.S. Cl. | 260/256.4 F; 260/256.5 R; 424/251 | |
| [51] | Int. Cl.² | C07D 487/04 | |
| [58] | Field of Search | 260/256.4 F, 256.5 R | |
| [56] | References Cited | | |
| | UNITED STATES PATENTS | | |
| 3,257,401 | 6/1966 | Wagner | 260/256.4 F |
| 3,600,390 | 8/1971 | Sherlock | 260/256.4 F |
| 3,621,025 | 11/1971 | Jen et al. | 260/256.4 F |
| 3,745,216 | 7/1973 | Jen et al. | 260/256.4 F |
| 3,790,576 | 2/1974 | De Wald | 260/286 R |
| 3,859,289 | 1/1975 | Hardtmann | 260/256.4 F |
| | FOREIGN PATENTS OR APPLICATIONS | | |
| 2,081,375 | 0000 | France | |
| 2,305,575 | 8/1973 | Germany | |

OTHER PUBLICATIONS

Bernardi, et al., "Chemical Abstracts", vol. 74, 1971, Col. 141859b.
Brown, *Heterocyclic Compounds*: Fused Pyrimidines, Part I, 1967, Wiley–Interscience, New York, pp. 222–225.

*Primary Examiner*—Nicholas S. Rizzo
*Assistant Examiner*—James H. Turnipseed
*Attorney, Agent, or Firm*—Robert E. Havranek

[57] ABSTRACT

A new process has been developed for the synthesis of optionally substituted 1,2,3,5-tetrahydroimidazo[2,1-b]quinazolin-2-ones.

4 Claims, No Drawings

PROCESS FOR THE PREPARATION OF OPTIONALLY SUBSTITUTED 1,2,3,5-TETRAHYDROIMIDAZO[2,1-b] QUINAZOLIN-2-ONES

BACKGROUND OF THE INVENTION

1. Field of the Invention

The compounds of the present invention are useful in the control of mild to severe hypertension, as anti-clotting agents and, in some instances, bronchodilators.

2. Description of the Prior Art

The compounds of the present invention are new and novel and so is the process described herein. The literature discloses the following prior art:

A. The compounds characterized as 1- and 9-alkyl-2,3-dihydroimidazo-[1,2-a]-benzimidazoles [R. J. North and A. R. Day, J. Hetero. Chem., 655 (1969)]. The compounds have the following structure

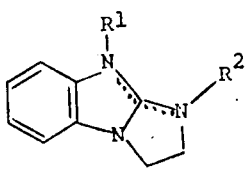

in which $R^1$ and $R^2$ are optionally substituted with alkyl functions.

B. B. Loev, T. Jen and R. A. McLean, Experientia, 27, 875 (1971) disclose the compound having the formula

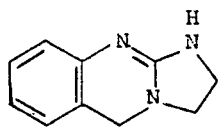

as having potent antihypertensive activity in rats, dogs, cats and rabbits.

C. R. Grout and M. Partridge, J. Chem. Soc., 3551 (1960) report the synthesis of the compound

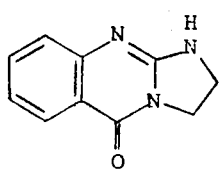

No antihypertensive activity was reported.

D. K. Lempert and G. Doleschall, Experientia, 18, 401 (1962) and Acta Chimica Academiae Scientiarum Hungaricae, 45, 357–68 (1965) report the synthesis of the compounds

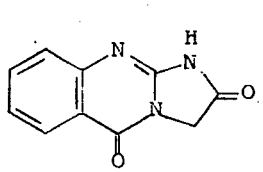

No antihypersensitive activity was reported.

E. A. Simonov et al., Khim. Farmatseut. Zh., (1969) [Annual Reports in Medicinal Chemistry, Chapt. 6, 53 (1969)] report the preparation of 9-substituted imidazobenzimidazoles having the formula

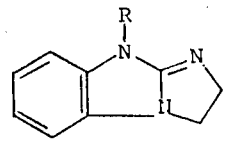

said compounds reported to have hypotensive effects in animals but no detailed data was presented.

F. G. E. Hardtmann, German Pat. No. 2,025,248 (1970) reports bronchodilating and hypotensive effects for the compounds having the formula

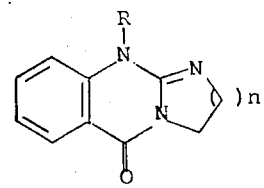

G. T. Jen et al., J. Med. Chem., 15 (7), 727–31 (1972) describe the compounds having the formula

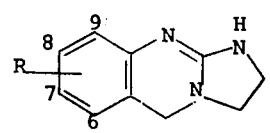

in which R is H, 6-Cl, 7-Cl, 7-MeO, 7-OH, 8-Cl, 9-Cl and 9-$CH_3$ as being hypotensive agents.

SUMMARY OF THE INVENTION

The compounds having the formula

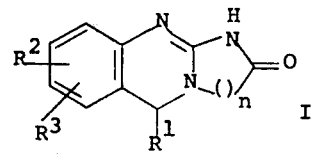

in which $R^1$ is H or (lower)alkyl of 1 to 6 carbon atoms, $R^2$ and $R^3$ are alike or different and are hydrogen, chloro, bromo, fluoro, $SO_3H$, $CF_3$, (lower)alkyl of 1 to 6 carbon atoms, hydroxy, nitro, amino, (lower)alkoxy or phenyl, or when taken together $R^2$ and $R^3$ are methylenedioxy or the residue of a phenyl ring, and n is an integer of 1 or 2; are prepared by the process which comprises the consecutive steps of A. mixing a compound having the formula

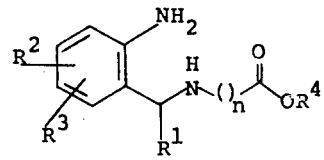

in which $R^1$, $R^2$ and $R^3$ are as described above, n is 1 or 2, and $R^4$ is (lower)alkyl of 1 to 6 carbon atoms, with a condensation agent selected from the group consisting of phosgene, thiophosgene and 1,1'-carbonyldiimidazole in a ratio of at least one mole of condensation agent per mole of II, in the presence of a reaction inert organic solvent with the aid of heat to produce the compound having the formula

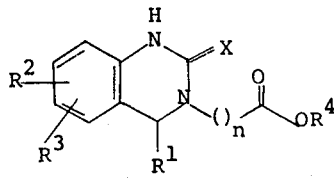   III in which n, $R^1$, $R^2$, $R^3$ and $R^4$ are as above and X is O or S;

B. treating compound III with a halogenating agent such as $POBr_3$, $POCl_3$, thionylchloride or a tri(lower)alkoxonium tetrafluoroborate when X is oxygen to produce the compound having the formula

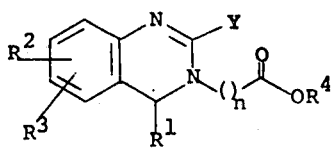   IVa in which n, $R^1$, $R^2$, $R^3$ and $R^4$ are as above and Y is Cl, Br or (lower)alkoxy, or when X is S, treating compound III with at least one mole of base, following which the resultant slurry is treated with an alkylating agent such as a (lower)alkyl halide, dimethylsulfate or methyl tosylate, etc., in which the halide is Cl, Br or I to produce the compound havng the formula

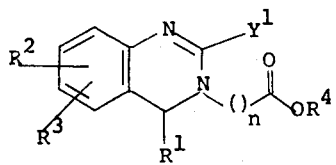   IVb in which n, $R^1$, $R^2$, $R^3$ and $R^4$ are as above and $Y^1$ is $-SR^5$ in which $R^5$ is (lower)alkyl; and C. treating compound IVa or IVb with a large excess of ammonia dissolved in a (lower)alkanol; preferably methanol, ethanol, n-propanol or isopropanol, with the aid of heat, to produce the compound I.

DETAILED DESCRIPTION

This invention relates to a new and improved process for the preparation of optionally substituted 1,2,3,5-tetrahydroimidazo[2,1-b]-quinazolin-2-ones having the formula

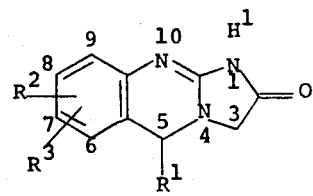   I in which $R^1$ is H or (lower)alkyl, $R^2$ and $R^3$ are alike or different and are hydrogen, chloro, bromo, fluoro, $CF_3$, $SO_3H$, (lower)alkyl, hydroxy, nitro, amino, (lower)alkoxy or phenyl, or when taken together $R^2$ and $R^3$ are methylenedioxy or the residue of a phenyl ring; or a pharmaceutically acceptable acid addition salt thereof.

Hypertension is a rather common and serious disease, particularly in elderly people. High blood pressure, a result of hypertension, is a common affliction. Most particularly, hypertension is often the cause of crippling or fatal strokes in the elderly. It was, therefore, an object of the present invention to provide compounds useful in the treatment of mild to severe hypertension.

Subsequent to the preparation of some of the compounds of the present invention, it was found that most of the compounds also possessed unique properties as blood platelet anti-aggregative agents. These compounds are useful in the prevention of intravascular thrombosis, prevention of coronary thrombosis, prevention of transient ischemic episodes, prevention of platelet thrombosis in the use of prosthetic devices (artificial heart valves, etc.). A large number of compounds of the present invention have also been found to possess desirable bronchodilator activity in mammals.

For the purpose of this disclosure, the compounds of the present invention are represented as having the formula I. However, compounds can exist in several possible tautomeric forms; e.g.:

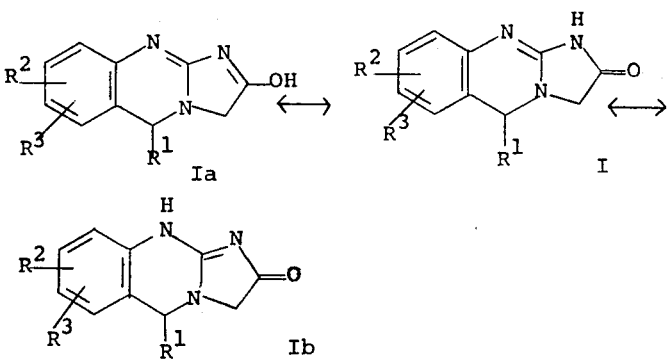

All the possible tautomers are considered an integral part of the present invention and all these forms are considered included when the compounds are represented as formula I.

The nontoxic salts that are pharmaceutically acceptable include the hydrochlorides, hydrobromides, hydroiodides, (lower)alkylsulfates, (lower)alkyl and aryl sulfonates, phosphates, sulfates, maleates, fumarates, succinates, tartrates, citrates, and other commonly used in the art.

The salts obtained through the variation of the acid used in some cases have special advantage due to increased stability, increased solubility, decreases solubility, ease of crystallization, lack of objectionable taste, etc., but these are all subsidiary to the main physiological action of the free base, which is independent of the character of the acid used in the preparation of the salt.

Diagramatically, the process of the instant invention is as follows:

in which $R^1$, $R^2$, $R^3$ and $R^4$ are as above.

In certain cases, particularly when $R^2$ or $R^3$ is a bromine or $NO_2$, it may be desirable to brominate or nitrate after producing compound I.

A preferred embodiment of the present invention is the process for the synthesis of compounds having the formula

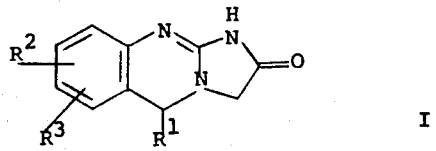

I in which $R^1$ is H or (lower)alkyl, $R^2$ and $R^3$ are alike or different and are hydrogen, chloro, bromo, fluoro, (lower)alkyl, hydroxy, nitro, $SO_3H$, amino, (lower)alkoxy or phenyl, or when taken together $R^2$ and $R^3$ are methylenedioxy or the residue of a phenyl ring; which comprises the consecutive steps of

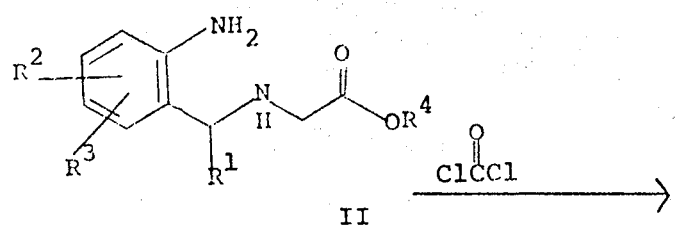

II

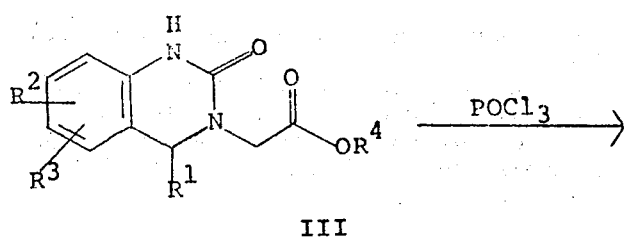

III

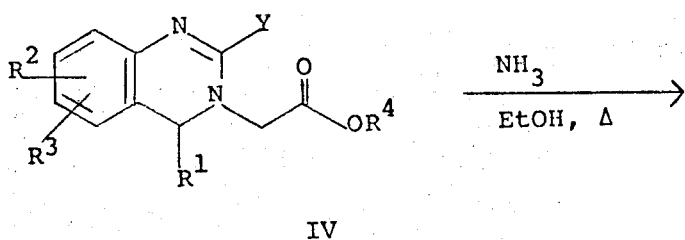

IV

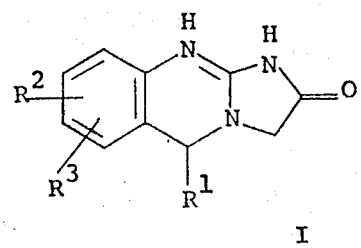

I

A. mixing a compound having the formula

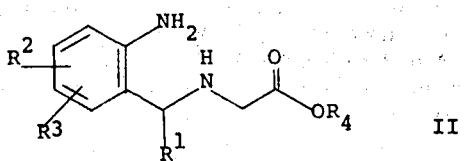

II in which R¹, R² and R³ are as described above and R⁴ is (lower)alkyl of 1 to 6 carbon atoms, with a condensation agent selected from the group consisting of phosgene, thiophosgene and 1,1′-carbonyldiimidazole in a ratio of at least one mole of condensation agent per mole of compound II, in the presence of a reaction inert organic solvent with the aid of heat, to produce the compound having the formula

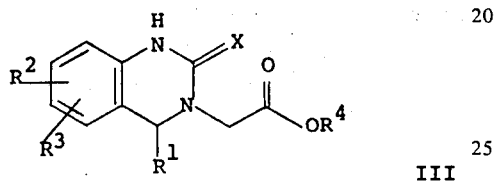

III in which R¹, R², R³ and R⁴ are as above and X is O or S;

B. treating compound III with at least one mole of POCl₃, SOCl₂, POBr₃, or tri(lower) alkoxonium tetrafluoroborate when X is oxygen to produce the compound having the formula

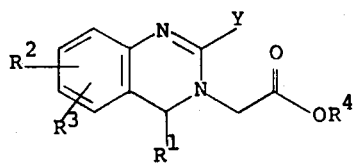

IVa in which R¹, R², R³ and R⁴ are as above and Y is Br, Cl or (lower)alkoxy, or when X is S, treating compound III with an excess of strong base in a reaction inert organic solvent, following which the resultant slurry is treated with a (lower)alkyl halide, dimethylsulfate, methyl tosylate, etc. in which the halide to produce the compound having the formula

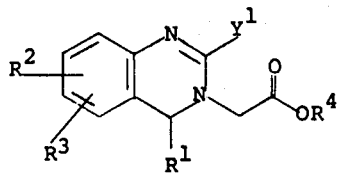

IVb in which R¹, R², R³ and R⁴ are as above and Y¹ is S-R⁵ on which R⁵ is (lower)alkyl; and C. treating compound IVa or IVb with a large excess of ammonia dissolved in a (lower)alkanol selected from the group consisting of methanol, ethanol, n-propanol and isopropanol with the aid of heat, to produce the compound I.

A more preferred embodiment is the process for the preparation of compounds having formula I, which process comprises the consecutive steps of A. mixing a compound having the formula

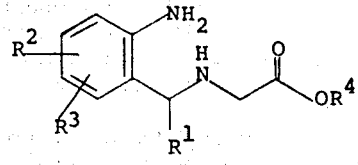

II in which R¹, R² and R³ are as described above and R⁴ is (lower)alkyl of 1 to 4 carbon atoms with a condensation agent selected from the group of phosgene, thiophosgene and 1,1′carbonyldiimidazole in a ratio of about 1 to 1.5 moles of condensation agent per mole of compound II, in the presence of a reaction inert organic solvent selected from the group consisting of tetrahydrofuran, dioxane, benzene, toluene, xylene, diethyl ether, dibutylether and the like, with the aid of heat to produce the compound having the formula

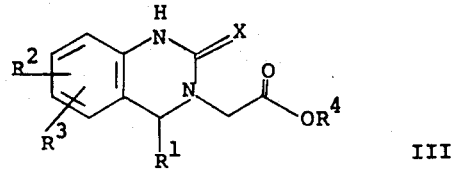

III in which R¹, R², R³ and R⁴ are as above and X is O or S;

B. treating compound III with POCl₃, SOCl₂ or triethoxonium tetrafluoroborate when X is oxygen in a ratio of about 1 to 10 moles of reagent per mole of compound III to produce the compound having the formula

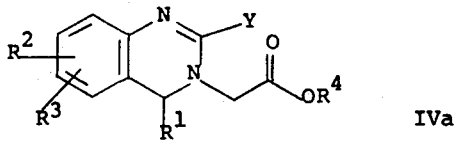

IVa in which R¹, R², R³ and R⁴ are as above and Y is Cl or —OC₂H₅, or when X is S, treating one mole of compound III with about 1 to 4 moles of a strong base selected from the group consisting of sodium hydride, sodium hydroxide, sodium or potassium (lower)alkoxide, or potassium hydroxide in a reaction inert organic solvent selected from the group consisting of benzene, toluene, xylene, tetrahydrofuran, dioxane, diethyl ether and the like, following which the resultant slurry is treated with a (lower)alkyl halide in which the halide is Cl, Br or I, in a ratio of 1.5 to 6 moles of alkyl halide per mole of compound III, to produce the compound

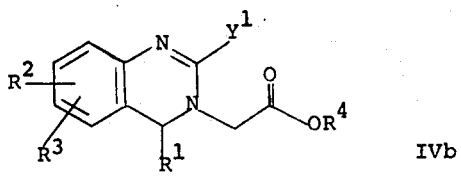

IVb in which $R^1$, $R^2$, $R^3$ and $R^4$ are as above and $Y^1$ is $-SR^5$ in which $R^5$ is (lower)alkyl; and C. treating compound IVa or IVb with a large excess of ammonia dissolved in a (lower)alkanol selected from the group consisting of methanol, ethanol, n-propanol and isopropanol, with the aid of heat, in a sealed vessel, to produce the compound I.

A most preferred embodiment is the process for the preparation of compounds having formula I, which process comprises the consecutive steps of A. mixing a compound having the formula

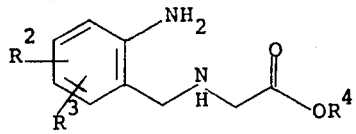

II in which $R^2$ and $R^3$ are as described above and $R^4$ is (lower)alkyl of 1 or 2 carbon atoms, with a condensation agent selected from the group consisting of 1,1'-carbonyldiimidazole, phosgene or thiophosgene in a ratio of about 1 to 1.3 moles of condensation agent per mole of compound II, in the presence of a reaction inert solvent selected from the group consisting of tetrahydrofuran or dioxane at about $-10°$ C to $+5°$ C, followed by heating at reflux temperatures to produce the compound having the formula

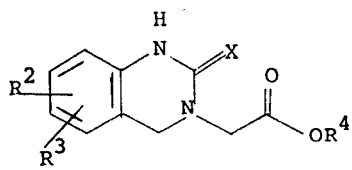

III in which $R^2$, $R^3$ and $R^4$ are as above and X is O or S;

B. treating compound III with $POCl_3$ or thionyl chloride when X is oxygen in a ratio of about 2 to 6 moles of $POCl_3$ or thionyl chloride per mole of compound III, with or without the presence of a reaction inert organic solvent selected from the group consisting of benzene, toluene, xylene, tetrahydrofuran, diethyl ether, dipropyl ether, dibutylether and dioxane, with the aid of heat, to produce the compound having the formula

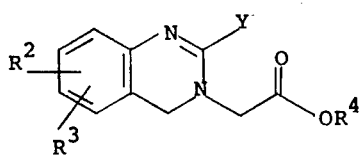

IVa in which $R^2$, $R^3$ and $R^4$ are as above and Y is Cl, or when X is S, treating one mole of compound III with about 1 to 3 moles of sodium hydride in a reaction inert organic solvent selected from the group consisting of benzene, toluene, xylene, tetrahydrofuran, dioxane and diethyl ether, following which the resultant slurry is treated with methyl or ethyl halide in which the halide is Cl, Br or I, in a ratio of 1.2 to 3.6 moles of alkyl halide per mole of compound III, to produce the compound having the formula

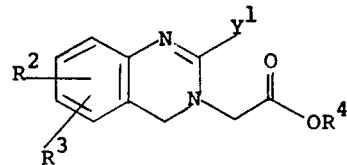

IVb in which $R^2$, $R^3$ and $R^4$ are as above and $Y^1$ is $-SCH_3$ or $-SC_2H_5$; and c. treating compound IVa or IVb with a large excess of ammonia dissolved in a (lower)alkanol selected from the group consisting of methanol, ethanol, n-propanol and isopropanol, with the aid of heat, in a sealed vessel, to produce the compound I.

The most preferred embodiment is the process for the preparation of compounds having the formula I, which process comprises the consecutive steps of A. mixing a compound having the formula

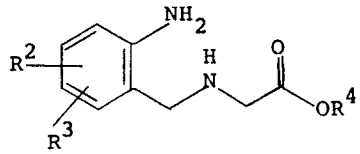

II in which $R^2$ and $R^3$ are as described above and $R^4$ is ethyl with 1,1'-carbonyldiimidazole in a ratio of about 1 to 1.2 moles of 1,1'-carbonyldiimidazole per mole of compound II, in the presence of tetrahydrofuran, at about $-5°$ C to $+5°$ C, followed by heating at reflux temperature for up to 18 hours to produce the compound having the formula

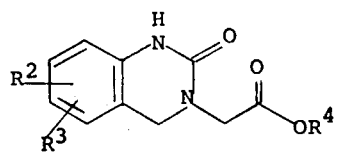

IIIa;

B. dissolving compound IIIa in $POCl_3$ or $POCl_3$ dissolved in a reaction inert organic solvent selected from the group consisting of benzene, toluene, tetrahydrofuran and dioxane, in a ratio of about 2 to 6 moles of $POCl_3$ per mole of compound IIIa, with the aid of heat to produce the compound having the formula

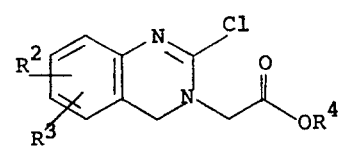

IVa in which $R^2$, $R^3$ and $R^4$ are as above; and

C. treating compound IVa with a large excess of ammonia dissolved in ethanol, at about +70° C to +130° C, in a sealed vessel, to produce the compound I.

For the purpose of this disclosure, the term (lower)alkyl shall mean straight and branched chain saturated aliphatic groups having 1 to 6 carbons inclusive unless designated otherwise. The term (lower)alkanol or (lower)alkoxy shall have the same connotation, an alcohol or alkoxy group of 1 to 6 carbons inclusive.

Pharmacological evaluation has indicated the compounds produced by the present invention possess hypotensive activity.

The blood pressure of unanesthetized rats and dogs was measured directly by means of a transducer attached to an intra-arterial cannula and in anesthetized dogs by a mercury manometer attached to a carotid cannula.

The compounds of the instant invention were tested as the hydrochloride salts by the above method in genetically hypertensive rats in doses of 50 mg./kg. orally.

At the present time, indications are that the compounds do not appear to be acting in the same way as 2-(2,6-dichloroanilino)-2-imidazoline hydrochloride ["CATAPRES"]. Their activity is probably not attributable to α-adrenergic blockade or to ganglionic blocking action.

In the treatment of hypertension in animals including man, the compounds of the present invention are administered orally and/or parenterally, in accordance with conventional procedures for the administration of hypotensive agents in an amount of from about 0.5 mg./kg./ dose to 30 mg./kg./dose depending upon the route of administration and the particular compound of the invention. The preferred dosage for the compounds of the invention is in the range of about 1.0 to 15.0 mg./kg./ dose two to four times a day.

Pharmacological evaluation has also indicated the compounds of the present invention possess blood platelet anti-aggregative activity.

The aggregometer method of Born (1), as modified by Mustard, et al. (2) was used to assess the in vitro activity of the various compounds as to inhibition of adenosine diphosphate (ADP) and collagen-induced platelet aggregation. Platelet rich plasma was separated by centrifugation from citrated (3.8 per cent) rabbit blood. ADP in final concentration of 0.5 mcg./ml. or 0.05 ml. of a collagen suspension prepared according to the method described by Evans et al. (3) was used to induce aggregation. The various compounds tested were dissolved in dimethylsulfoxide (DMSO) so that 5 mcl. added to the platelet rich plasma would yield the desired test concentration. Vehicle control trails were done and compared with aggregation induced in platelet rich plasma containing various concentrations of the test compounds. Dose response curves were obtained and Effective Concentration (EC50) values calculated.

1. Born, G. V. R. J. Physiol., London, 162 67P (1962).
2. Mustard, J. F., Hegardt, B. Rowsell, H. C. and MacMillan, R. L., J. Lab. Clin. M-d. 54, 548 (1964).
3. Evans, G. Marian, M. C., Packham, M. A., Nishizawa, E. E., Mustard, J. F. and Murphy, E. A., J. Exp. Med., 128, 877 (1968).

Table I is illustrative of the hypotensive and blood platelet anti-aggregative activity of some of the preferred embodiments of the present invention.

TABLE I

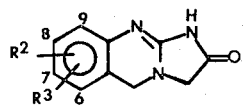

| Compound No. | R Position 6 | 7 | 8 | 9 | Blood Pressure % Change Rats P.O. 50 mg./kg. | In Vitro EC50 (mg./ml.) ADP | Collagen | In Vivo/In Vitro* Rabbits I.P. ED50 (mg./kg.) ADP | Dogs P.O. 5 mg./kg. ADP % Inhibition |
|---|---|---|---|---|---|---|---|---|---|
| 1 | H | H | H | H | −36±6 | 6 | 2 | >72 | |
| 2 | Cl | H | H | H | −37±8 | 1 | 0.02 | 2 | |
| 3 | H | Cl | H | H | −4±5 | 0.5 | 0.2 | >10 | |
| 4 | H | H | Cl | H | −14 | 6 | 1.5 | 18 | |
| 5 | H | H | H | Cl | −10±1 | 7 | 0.3 | 6 | |
| 6 | H | Br | H | H | −8±3 | 0.4 | 0.2 | 5 | |
| 7 | H | H | F | H | −27±3 | 6 | 2 | >10 | |
| 8 | H | NO₂ | H | H | 5±2 | 2 | 0.2 | >10 | |
| 9 | H | NH₂ | H | H | −10±14 | 50 | 6 | | |
| 10 | CH₃ | H | H | H | −37±8 | 0.5 | 0.1 | 0.6 | 76 |
| 11 | H | CH₃ | H | H | | 2 | 0.3 | >10 | |
| 12 | H | H | H | CH₃ | −22±10 | 4 | 3 | >10 | |
| 13 | OME | H | H | H | −20±14 | 0.5 | 0.2 | 4 | 19 |
| 14 | H | OME | H | H | −19±4 | 1 | 0.2 | 4 | 17 |
| 15 | H | H | H | OME | −16±3 | NA | NA | | |
| 16 | OME | OME | H | H | | 0.4 | | 0.7 | |
| 17 | H | OME | OME | H | +26 | 5 | | 4 | 0 |
| 18 | H | O⌒O | | H | −25±12 | 0.7 | 0.07 | >50 | |
| 39 | —CH=CH—CH=CH— | | H | H | −59 | — | — | — | — |

TABLE I-continued

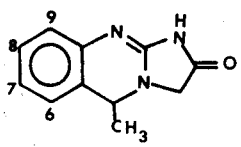

| | R Position | | | | | | |
|---|---|---|---|---|---|---|---|
| | 6 | 7 | 8 | 9 | | | |
| 29 | H | H | H | H | −28 | 2 | 7 | 35 |
| 50 | CH₃ | H | H | H | −49 | | | |
| 51 | H | CH₃ | H | H | −34 | | | |

+Denotes an increase in b.p.
−Denotes a decrease in b.p.

*In vivo/In vitro testing:

Before dosing the animals, blood samples are taken. The blood is centrifuged to obtain the blood platelet-rich plasma. Aggregation of this plasma is induced with ADP or collagen. This is the control.

The animals are then dosed with the compounds to be tested (orally or parenterally). Depending upon the route of administration, one to two hours are allowed to elapse after dosing. Blood is drawn and the same procedure employed as for the control is untreated animals.

The dose required to produce 50% inhibition of the aggregation is determined by dose response data obtained in this manner.

Starting Materials

All products described are supported by satisfactory infrared (IR) and nuclear magnetic resonance (nmr) spectra. Melting points are uncorrected. Temperatures are expressed in degrees Centigrade (°C.) and pressures in millimeters of mercury (mm).

A. Preparation of N-(o-Nitrobenzyl)ethyl glycine

To a suspension of 55.9 g. (4.0 × 10$^{-1}$ moles) of ethyl glycine hydrochloride in 300 ml. of absolute ethyl alcohol was slowly added (~5 minutes) under a nitrogen atmosphere a solution of 70 ml. (5.0 × 10$^{-1}$ moles) of triethylamine in 200 ml. of absolute ethyl alcohol.

The mixture was heated to reflux and a solution of 17.2 g. (1.0 × 10$^{-1}$ moles) o-nitrobenzylchloride in 200 ml. of absolute ethyl alcohol was added over a 1.5 hour period. Upon complete addition, the mixture was allowed to reflux for 18 hours, cooled to room temperature and the solvent removed in vacuo. To the solid residue was added 500 ml. of water and enough 10% hydrochloric acid to make the solution acidic (pH~3).

The acidic solution was washed with methylene chloride (2 × 150 ml.), made neutral (pH~7) by the addition of saturated sodium bicarbonate and the insoluble oil extracted with methylene chloride (2 × 250 ml). The methylene chloride extracts were combined, washed with water (250 ml.), dried (K₂CO₃) and the solvent removed in vacuo resulting in a yellow oil. Owing to the instability of the oil toward distillation, the compound was used as such in subsequent reaction.

B. Preparation of N-(o-Aminobenzyl)ethyl glycine

To a solution of 13.0 g. (5.46 × 10$^{-2}$ moles) of N-(o-nitrobenzyl)ethyl glycine in 200 ml. of absolute ethyl alcohol was added slowly 0.76 g. (5% by weight) of 10% Pd/C catalyst and the mixture placed on a Paar hydrogenator. The mixture was shaken until theoretical hydrogen (16.4 × 10$^{-2}$ moles) had been absorbed, removed from the Paar and the mixture filtered under suction. The catalyst was washed with ethyl alcohol and the solvent removed in vacuo affording a yellow oil. Purification of the oil was effected by distillation yielding 8.8 g. (77% yield) of a colorless oil; b.p. 124°–126° C. (0.03 mm).

Anal. calc'd. for C₁₁H₁₆N₂O₂: C, 63.44; H, 7.74, N, 13.45. Found: C, 63.57; H, 7.89; N, 13.57.

C.

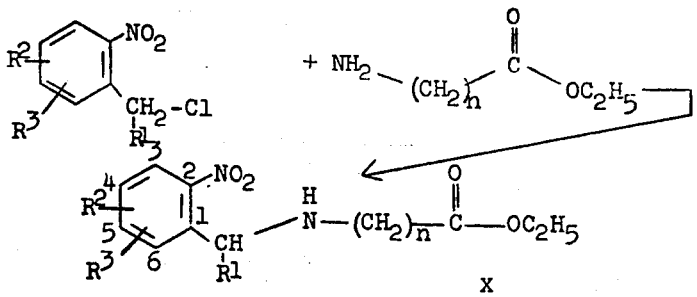

Preparation of Substituted N-(o-Nitrobenzyl)-Ethyl Glycinates

Substitution in the procedure of A supra for the o-nitrobenzyl chloride used therein of an equimolar quantity of the appropriately R¹,R², R³-substituted o-nitrobenzylchloride produced the compounds having formula X in which n, R¹, R² and R³ are as designated:

| Compound No. | R¹ | R² | R³ | n |
|---|---|---|---|---|
| 2A | H | H | 6-Cl | 1 |
| 3A | H | H | 5-Cl | 1 |
| 4A | H | H | 4-Cl | 1 |
| 5A | H | H | 3-Cl | 1 |
| 7A | H | H | 4-F | 1 |
| 10A | H | H | 6-CH₃ | 1 |
| 11A | H | H | 5-CH₃ | 1 |
| 12A | H | H | 3-CH₃ | 1 |
| 13A | H | H | 6-OCH₃ | 1 |
| 14A | H | H | 5-OCH₃ | 1 |
| 15A | H | H | 3-OCH₃ | 1 |
| 16A | H | 5-OCH₃ | 6-OCH₃ | 1 |
| 17A | H | 4-OCH₃ | 5-OCH₃ | 1 |
| 18A | H | R² and R³ are methylenedioxy | | 1 |
| 29A | CH₃ | H | H | 1 |
| 31A | H | 3-CH₃ | 6-CH₃ | 1 |
| 32A | H | H | 6-Br | 1 |
| 33A | H | H | 6-F | 1 |

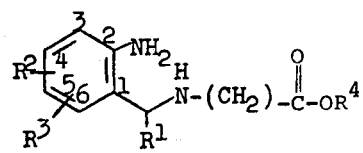

II

Substitution in the procedure of B supra of the N-(o-nitrobenzyl)ethylglycine used therein of an equimolar quantity of the appropriately $R^1$, $R^2$, $R^4$, $R^3$-substituted compound III produced the compounds having the formula II.

| Compound No. | n | R¹ | R² | R³ | R⁴ | b.p. (mm.) | % yield |
|---|---|---|---|---|---|---|---|
| 2B | 1 | H | H | 6-Cl | Et | **m.p. 185–186°C. as 2 . HCl | *80% crude |
| 3B | 1 | H | H | 5-Cl | Et | ** | * |
| 4B | 1 | H | H | 4-Cl | Et | ** | * |
| 5B | 1 | H | H | 3-Cl | Et | ** | * |
| 7B | 1 | H | H | 4-F | Et | 138°C. (0.35) | *63 (crude) |
| 10B | 1 | H | H | 6-CH₃ | Et | 170°C. (0.3) | |
| 11B | 1 | H | H | 5-CH₃ | Et | 129–133°C. (0.1) | |
| 13B | 1 | H | H | 6-OCH₃ | Et | ** | |
| 14B | 1 | H | H | 5-OCH₃ | Et | 162–164°C. (0.3) | 98 (crude) |
| 15B | 1 | H | H | 3-OCH₃ | Et | ** | |
| 16B | 1 | H | 5-OCH₃ | 5-OCH₃ | Et | ** | |
| 17B | 1 | H | 4-OCH₃ | 6-OCH₃ | Et | *m.p. 202–203°C. | 93 (crude) |
| 18B | 1 | H | R² and R³ are methylenedioxy | | Et | ** | 99 (crude) |
| 31B | 1 | H | 3-CH₃ | 6-CH₃ | Et | ** | 92 |
| 32B | 1 | H | H | 6-F | Et | ** | 74 |
| 33B | 1 | H | H | 4-CF₃ | Et | M.P. 182–3°C. | 78 |
| 34B | 1 | H | H | 4-CH₃ | Et | ** | 97 |
| 35B | 1 | H | 4-CH₃ | 6-CH₃ | Et | ** | 88 |
| 36B | 1 | H | 4-CH₃ | 5-CH₃ | Et | ** | 91 |
| 37B | 1 | H | 5-CH₃ | 6-CH₃ | Et | ** | 99 |
| 38B | 1 | H | H | 6-Et | Et | ** | 90 |
| 39B | 1 | H | 5,6-CH=CH—CH=CH— | | Et | ** | 92 |
| 40B | 1 | H | 4-Cl | 6-Cl | Et | ** | 92 |
| 41B | 1 | H | 3-Cl | 6-Cl | Et | ** | |
| 42B | 1 | H | H | 6-Br | Et | ** | 74 |
| 43B | 1 | H | H | 6-CF₃ | Et | ** | |

*These reductions were carried out in the presence of two equivalents of hydrochloric acid.
**Compounds could not be distilled; used crude in subsequent reactions.

D.

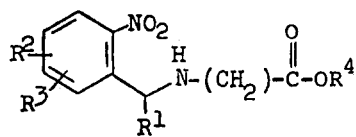

X

DESCRIPTION OF THE PREFERRED EMBODIMENTS

EXAMPLE 1

Preparation of 5-methyl-3-(carbethoxymethyl)-1,2,3,4-tetrahydroquinazolin-2-one (IIIc)

To a cooled solution of 15.00 g (67 mmole) of N-(2-amino-6-methylbenzyl) glycine ethyl ester (10b) in 300 ml of anhydrous tetrahydrofuran under a nitrogen atmosphere was added a solution of 11.72 g (72 mmole) of 1,1'-carbonyldiimidazole in 200 ml of anhydrous tetrahydrofuran at such a rate that the temperature did not exceed 5°. Upon complete addition, the solution was allowed to stir at room temperature for 2 hrs., heated to reflux for 18 hrs., cooled to room temperature and the tetrahydrofuran removed in vacuo. The residue was dissolved in methylene chloride (250 ml), washed with 5% aqueous hydrochloric acid (2×100 ml), then water (100 ml). The methylene chloride extract was dried ($Na_2SO_4$) and the solvent removed in vacuo affording 14.0 g (83% yield) of a colorless solid. Purification was effected by crystallization from nitromethane; m.p. 184°–5°.

Anal. calc'd. for $C_{13}H_{16}N_2O_3$: C, 62.89; H, 6.50; N, 11.28. Found: C, 62.85; H, 6.45; N, 11.22.

EXAMPLE 2

Preparation of 2-Chloro-3-carbethoxymethyl-5-methyl-3,4-dihydroquinazoline hydrochloride (IV ac)

A mixture of 2.45 g (10 mmole) of 5-methyl-3-carbethoxymethyl-1,2,3,4-tetrahydroquinazolin-2-one (IIIc) and 20 ml of phosphorus oxychloride was immersed in an oil bath (105°–110°) for 3.5 hr. The solution was cooled, the excess phosphorus oxychloride removed under aspirator pressure and the residue dissolved in chloroform (50 ml). Ice water was added, the mixture shaken and 40% sodium hydroxide was added dropwise to attain a pH=6. The above process was repeated until a pH=6 was maintained after shaking, the chloroform extract was separated, dried ($Na_2SO_4$) and the solvent removed in vacuo. The residue was dissolved in ethyl acetate (100 ml), the solution saturated with hydrogen chloride gas and the mixture heated to gentle boiling for 10 mins. The mixture was filtered while hot and the precipitate dried yielding 2.11 g (70% yield) of a pale yellow powder. Purification was effected by crystallization from acetonitrile; mp 199–201.

Anal. calc'd. for $C_{13}H_{15}ClN_2O_2 \cdot HCl$: C, 51.52; H, 5.28; N, 9.24. Found: C, 51.87; H, 5.28; N, 9.27.

EXAMPLE 3

Preparation of 6-methyl-1,2,3,5-tetrahydroimidazo-[2,1-b]quinazolin-2-one [(10)-(Ic)]

To a solution of 0.60 g (2 mmole) of IVac in 20 ml of absolute ethyl alcohol was added 1.36 g (4 mmole) of a 5% ammonia ethyl alcohol stock solution, the system stoppered and immersed in an oil bath (100°). After 16 hrs. of heating, the solution was cooled, the solvent removed in vacuo and the residue suspended in water (30 ml). The mixture was made basic (pH9) by the addition of saturated sodium bicarbonate solution, the mixture stirred at room temperature and filtered. The precipitate was washed with water, then isopropyl alcohol and dried yielding 0.32 g (80% yield) of a colorless powder. The spectral properties (ir and nmr) were indentical to the known 6-methyl-1,2,3,5-tetrahydroimidazo[2,1-b]quinazolin-2-one (Ic); m.p. 250° C. >250° C.

Anal. calc'd. for $C_{11}H_{11}N_3O \cdot HCl \cdot 1/2H_2O$: C, 52.91; H, 5.25; N, 16.83; Cl, 14.20. Found: C, 53.20; H, 5.28; N, 17.00; Cl, 14.28.

EXAMPLE 4

Preparation of 5-methyl-3-(carbethoxymethyl)-1,2,3,4-tetrahydroquinazolin-2-thione (IIId)

To a cooled solution of compound (10b) (15 g., 67 mmole) in 300 ml of anhydrous tetrahydrofuran under a nitrogen atmosphere, is added 72 mmole of thiophosgene at about room temperature. Upon completion of the addition, the solution was refluxed for 10 hours, cooled to room temperature and the tetrahydrofuran removed in vacuo. The residue is dissolved in methylene chloride, washed with 5% aqueous hydrochloric acid, then water. The methylene chloride solution is dried over sodium sulfate, filtered and the solvent removed in vacuo to produce the title product.

EXAMPLE 5

Preparation of 3-Carbethoxymethyl-5-methyl-3,4-dihydroquinazoline-2-thiol methyl ether hydrochloride (IVbd)

A mixture of 2.45 g. (10 mmole) of 5-methyl-3-carbethoxymethyl-1,2,3,4-tetrahydroquinazolin-2-thione (IIId) and 20 mmoles of sodium hydride in benzene are stirred at room temperature for about 30 minutes and then warmed to 50° C. for 1 hour. The slurry is cooled to room temperature and 30 mmoles of methyl iodide is added with stirring, following which the mixture is again heated to 50° C. for another hour. The mixture is cautiously treated with water, the benzene layer separated, washed with water several times and then dried over sodium sulfate. The benzene is removed in vacuo to produce the title thiol methyl ether.

EXAMPLE 6

Preparation of 6-methyl-1,2,3,5-tetrahydroimidazo-[2,1-b]quinazolin-2-one [(10)-(Ic)]

Substitution in the procedure of example 3 for the IVac used therein of an equimolar quantity of IVbd produces the title product Ic.

EXAMPLE 7

Preparation of 5-methyl-3-(carbethoxymethyl)-1,2,3,4-tetrahydroquinazolin-2-one (IIIc)

Substitution in the procedure of example 1 for the 1,1'-carbonyldiimidazole used therein of an equimolar quantity of phosgene produces compound IIIc.

EXAMPLE 8

Preparation of 4,5-dimethyl-3-(carbethoxymethyl)-1,2,3,4-tetrahydroquinazoline-2-one (IIIe)

Substitution in the procedure of example 1 for the N-(2-amino-6-methylbenzyl)glycine ethyl ester used therein of an equimolar quantity of N-(2-amino-2,6-dimethylbenzyl)glycine ethyl ester produces the title compound IIIe.

EXAMPLE 9

Preparation of 2-Chloro-3-carbethoxymethyl-4,5-dimethyl-3,4-dihydroquinazoline hydrochloride (IVae)

Substitution in the procedure of example 2 for the compound IIIc used therein of an equimolar quantity of IIIe produces the title compound.

EXAMPLE 10

Preparation of 5,6-dimethyl-1,2,3,5-tetrahydroimidazo[2,1-b]quinazolin-2-one [(50)-(Ie)]

Substitution in the procedure of example 3 for the compound IVac used therein of an equimolar quantity of IVae produces compound Ie.

We claim:

1. The process for the preparation of a compound having the formula

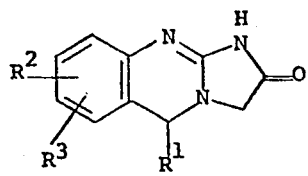

I in which $R^1$ is H or (lower)alkyl, $R^2$ and $R^3$ are alike or different and are hydrogen, chloro, bromo, fluoro, (lower)alkyl, hydroxy, nitro, $SO_3H$, amino, (lower)alkoxy or phenyl, or when taken together $R^2$ and $R^3$ are methylenedioxy or the moiety —CH=CH—CH=CH—; which process comprises the consecutive steps of A. mixing a compound having the formula

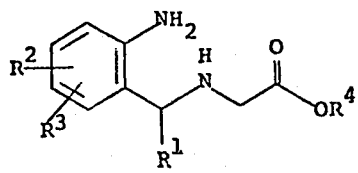

II in which $R^1$, $R^2$ and $R^3$ are as described above and $R^4$ is (lower)alkyl of 1 to 6 carbon atoms, with a condensation agent selected from phosgene and 1,1'-carbonyl diimidazole, in a ratio of at least one mole of condensation agent per mole of compound II, in the presence of a reaction inert organic solvent, with the aid of heat, to produce the compound having the formula

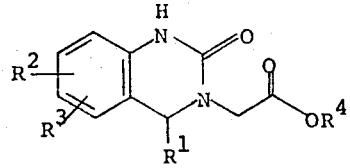

III in which $R^1$, $R^2$, $R^3$ and $R^4$ are as above,

B. treating compound III with at least one mole of $POCl_3$, $SOCl_2$, $POBr_3$ or tri(lower)alkoxonium tetrafluoroborate to produce the compound having the formula

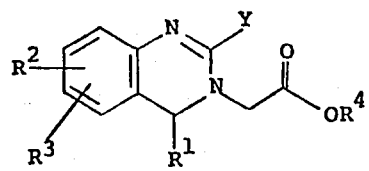

IVa in $R^1$, $R^2$, $R^3$ and $R^4$ are as above and Y is Cl, Br, or (lower)alkoxy; and C. treating compound IVa with a large excess of ammonia dissolved in a (lower)alkanol selected from the group consisting of methanol, ethanol, n-propanol and isopropanol with the aid of heat, to produce compound I.

2. The process of claim 1, which comprises the consecutive steps of

A. mixing a compound having the formula

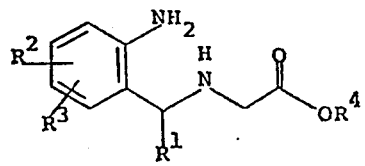

II in which $R^1$, $R^2$ and $R^3$ are as described and $R^4$ is (lower)alkyl of 1 to 4 carbon atoms, with a condensation agent selected from phosgene, and 1,1'-carbonyldiimidazole in a ratio of about 1 to 1.5 moles of condensation agent per mole of compound II, in the presence of a reaction inert organic solvent selected from the group consisting of tetrahydrofuran, dioxane, benzene, toluene, xylene, diethyl ether, dipropylether, diisopropylether, glyme, diglyme and dibutylether with the aid of heat to produce the compound having the formula

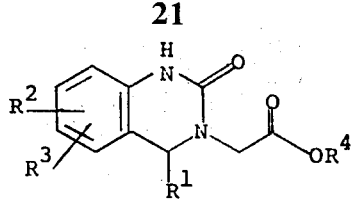

III in which $R^1$, $R^2$, $R^3$ and $R^4$ are as above;

B. treating compound III with $POCl_3$, $SOCl_2$ or triethoxonium tetrafluoroborate in a ratio of about 1 to 10 moles of reagent per mole of compound III to produce the compound having the formula

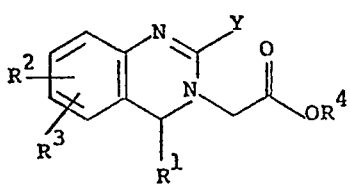

IVa in which $R^1$, $R^2$, $R^3$ and $R^4$ are as above and Y is Cl or $-OC_2H_5$; and C. treating compound IVa with a large excess of ammonia dissolved in a (lower)alkanol selected from the group consisting of methanol, ethanol, n-propanol and isopropanol, with the aid of heat, in a sealed vessel, to produce compound I.

3. The process of claim 1 which comprises the consecutive steps of

A. mixing a compound having the formula

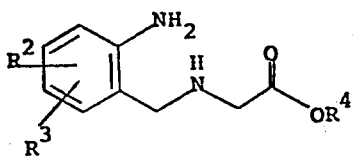

II in which $R^2$ and $R^3$ are as described and $R^4$ is (lower)alkyl of 1 or 2 carbon atoms, with a condensation agent selected from the group consisting of 1,1′-carbonyldiimidazole and phosgene in a ratio of about 1 to 1.3 moles of condensation agent per mole of compound II, in the presence of a reaction inert solvent selected from the group consisting of tetrahydrofuran or dioxane at about −10° C. to +5°C., followed by heating at reflux temperatures to produce the compound having the formula

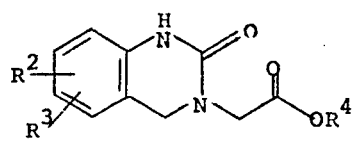

III in which $R^2$, $R^3$ and $R^4$ are as above;

B. treating compound III with $POCl_3$ or thionyl chloride in a ratio of about 2 to 6 moles of $POCl_3$ or thionyl chloride per mole of compound III, with or without the presence of a reaction inert organic solvent selected from the group consisting of benzene, toluene, xylene, tetrahydrofuran, diethyl ether, dipropyl ether, dibutylether and dioxane with the aid of heat, to produce the compound having the formula

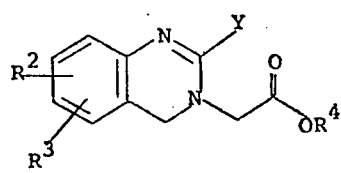

IVa in which $R^2$, $R^3$ and $R^4$ are as above and Y is Cl; and

C. treating compound IVa with a large excess of ammonia dissolved in a (lower)alkanol selected from the group consisting of methanol, ethanol, n-propanol and isopropanol, with the aid of heat, in a sealed vessel, to produce compound I.

4. The process of claim 1 which comprises the consecutive steps of

A. mixing a compound having the formula

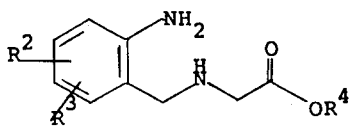

II in which $R^2$ and $R^3$ are as described and $R^4$ is ethyl, with 1,1′-carbonyldiimidazole in a ratio of about 1 to 1.2 moles of 1,1′-carbonyldiimidazole per mole of compound II, in the presence of tetrahydrofuran, at about −5° C to +5° C, followed by heating at reflux temperature for up to 20 hours to produce the compound having the formula

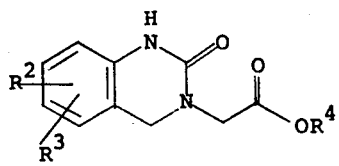

IIIa ;

B. dissolving compound IIIa in $POCl_3$ or $POCl_3$ dissolved in a reaction inert organic solvent selected from the group consisting of benzene, toluene, tetrahydrofuran, dioxane, in a ratio of about 2 to 6 moles of $POCl_3$ per mole of compound IIIa, with the aid of heat to produce the compound having the formula

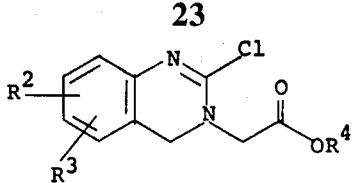
IVa
in which $R^2$, $R^3$ and $R^4$ are as above; and
C. treating compound IVa with a large excess of ammonia dissolved in ethanol, at about +70° C to +130°C, in a sealed vessel, to produce the compound I.
* * * * *